(12) United States Patent
Holdenrieder et al.

(10) Patent No.: US 7,229,772 B1
(45) Date of Patent: Jun. 12, 2007

(54) DETECTION OF APOPTOTIC PRODUCTS

(75) Inventors: Stefan Holdenrieder, Munich (DE); Martin Busch, Emmering (DE); Heinz Bodenmueller, Munich (DE); Georg Fertig, Penzberg (DE); Andreas Schalhorn, Planegg (DE); Petra Stieber, Gauting (DE)

(73) Assignee: Roche Diagnostics GmbH (DE)

( * ) Notice: Subject to any disclaimer, the term of this patent is extended or adjusted under 35 U.S.C. 154(b) by 0 days.

(21) Appl. No.: 09/646,409

(22) PCT Filed: Mar. 18, 1999

(86) PCT No.: PCT/EP99/01798

§ 371 (c)(1),
(2), (4) Date: Jun. 4, 2001

(87) PCT Pub. No.: WO99/47924

PCT Pub. Date: Sep. 23, 1999

Related U.S. Application Data

(60) Provisional application No. 60/079,494, filed on Mar. 26, 1998.

(30) Foreign Application Priority Data

Mar. 18, 1998 (DE) .................. 198 11 739

(51) Int. Cl.
*G01N 33/63* (2006.01)
*C12Q 1/68* (2006.01)
*C12P 19/34* (2006.01)
*A61K 39/395* (2006.01)
*C07H 21/02* (2006.01)
*C07H 21/04* (2006.01)

(52) U.S. Cl. .................. 435/7.1; 435/6; 435/91.1; 424/130.1; 536/23.1

(58) Field of Classification Search .................. 435/6, 435/7.1, 7.2, 7.5, 183, 975; 436/94; 536/23.1; 424/130.1, 178.1
See application file for complete search history.

(56) References Cited

U.S. PATENT DOCUMENTS

| 5,500,432 A | * | 3/1996 | Nicolaou et al. | 514/281 |
| 5,637,465 A | | 6/1997 | Trauth | 435/7.1 |
| 5,700,639 A | | 12/1997 | Trauth et al. | 435/6 |

FOREIGN PATENT DOCUMENTS

| WO | WO 93/09437 | 5/1993 |
| WO | WO 96/40985 | 12/1996 |
| WO | WO 97/35589 | 10/1997 |
| WO | WO 98/34118 | 8/1998 |

OTHER PUBLICATIONS

Haltiwanger et al., Characterization of class II apurinic/apyrimidinic endonuclease activities in the human malaria parasite, *Plasmodium falciparum*. Biochem. J., 345, 85-89, 2000.*

(Continued)

*Primary Examiner*—Frank Lu
(74) *Attorney, Agent, or Firm*—Barnes & Thornburg LLP

(57) ABSTRACT

The present invention concerns a method for the determination of apoptotic products in samples taken from patients in which apoptosis is induced as a result of disease or therapy, which is characterized in that the concentration of the apoptotic products in samples taken from patients is correlated with the effectiveness of the therapy and thus serves as a follow-up for the therapy. The serum samples are taken at various times and determined. The present invention in particular concerns a method in which the concentration of nucleosomes is determined in serum samples of tumour patients in order to assess the effectiveness of tumour therapy. Furthermore the present invention also concerns the use of a method according to the invention to determine the effectiveness of therapy in tumour patients who are subjected to a radiotherapy or chemotherapy treatment as well as in patients after an acute ischaemic event or after hypothermia treatment.

6 Claims, 17 Drawing Sheets

OTHER PUBLICATIONS

Figure 1:
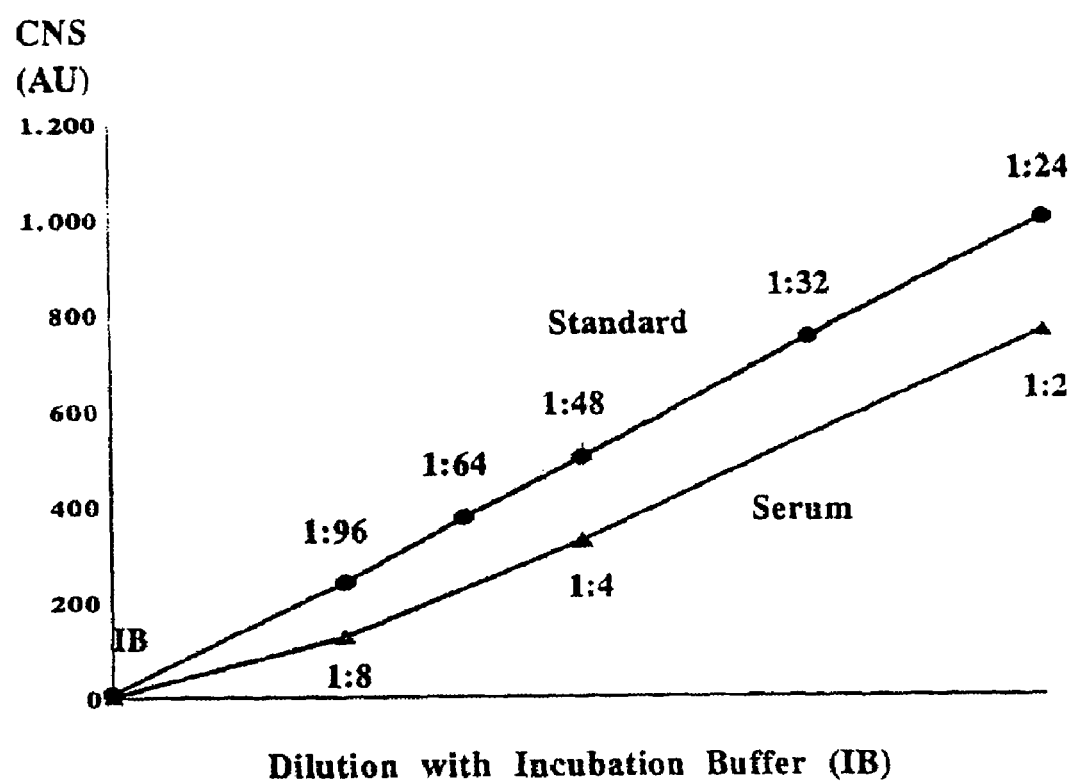

1997 Boehringer Mannheim Biochemicals Catalog, pp. 241 and 242. Published by Boehringer Mannheim Corporation, 9115 Hague Road, P.O. Box 50414, Indianapolis, IN 46250-0414.*

Rufus W. Burlingame, et al., "The Effect of Acute Phase Proteins on Clearance of Chromatin from the Circulation of Normal Mice" Copyright 1996 by The American Association of Immunologists p. 4783-4788.

S. Holdenrieder, et al., "Apoptosis in Serum of Patients with Solid Tumours" XXV ISOBM Meeting 1997, International Society for Oncodevelopmental Biology and Medicine in collaboration and Swiss Institute for Experimental Cancer Research (ISREC) Multidisciplinary Oncology Center (CPO) from Lausanne University Hospital (CHUV) From Basic Cancer Research to Clinical Applications, Montreux, Sep. 19-24, 1997.

P. Rumore, et al., "Haemodialysis as a model for studing endogenous plasma DNA: oligonucleosome-like structure and clearance" Clin. exp. Immunol. (1992) 90. 56-62.

V. Joyce Gauthier, et al., "Blood Clearance Kinetics and Liver Uptake of Mononucleosome in Mice" Copyright 1996 by the American Association of Immunologists, The Journal of Immunology, p. 1151-1156.

* cited by examiner

Fig. 13: Frequency distribution of the spontaneous nucleosome concentration in the serum

| | number > 500 (N.) AU | median (M) | mean (x) | standard deviation (σ) | ≤ 100 AU | > 100 AU | |
|---|---|---|---|---|---|---|---|
| healthy | 62<br>0 % | 24 | 34 | 32 | 96.8 % | 3.2 % | |
| patients with benign diseases | 108<br>% | 147 | 271 | 317 | 40.7 % | 59.3 % | 1 |
| benign pulmonary diseases | 13<br>% | 149 | 273 | 300 | 38.5 % | 61.5 % | |
| benign gastrointestinal diseases | 39<br>23.1 % | 94 | 281 | 349 | 51.3 % | 48.7 % | |
| benign gynaecological diseases | 37<br>10.8 % | 177 | 244 | 253 | 32.4 % | 67.6 % | |
| other benign diseases | 19<br>21.1 % | 139 | 303 | 362 | 36.8 % | 63.2 % | |
| pat. with malignant diseases | 337<br>24.6 % | 183 | 329 | 352 | 36.8 % | 63.2 % ü | |
| bronchial carcinomas | 38<br>36.8 % | 333 | 506 | 372 | 7.9 % | 92.1 % | |
| colorectal carcinomas | 60<br>21.7 % | 151 | 309 | 352 | 41.7 % | 58.3 % | |
| other gastrointestinal carcinomas | 44<br>22.7 % | 153 | 296 | 339 | 45.5 % | 54.5 % | |
| mammary carcinomas | 58<br>25.9 % | 191 | 339 | 329 | 24.1 % | 75.9 % | |
| ovarian carcinomas | 43<br>34.9 % | 233 | 407 | 371 | 27.9 % | 72.1 % | |
| other gynaecological carcinomas | 19<br>21.1 % | 191 | 351 | 397 | 31.6 % | 68.4 % | |
| ENT carcinomas | 8<br>12.5 % | 196 | 306 | 297 | 25.0 % | 75.0 % | |
| lymphomas | 16<br>37.5 % | 180 | 383 | 400 | 43.7 % | 56.3 % | |
| kidney cell carcinomas | 20<br>15.0 % | 60 | 194 | 248 | 60.6 % | 40.0 % | |
| prostate carcinomas | 17<br>0 % | 9 | 31 | 45 | 94.1 % | 5.9 % | |
| other carcinomas | 14<br>14.3 % | 144 | 228 | 228 | 50.0 % | 50.0 % | |

|  | remission N = 8 | No change N = 1 | progression N = 11 |
|---|---|---|---|
| kinetics of the basal nucleosome concentration |  |  |  |
| decrease > 50 % | 8 | 1 | 4 |
| no change | 0 | 0 | 1 |
| increase > 50 % | 0 | 0 | 6 |

Fig. 14: Correlation of the clinical course in patients during chemotherapy

Fig. 15: Correlation of the clinical course in patients during radiotherapy

|  | remission N = 10 | No change N = 1 | progression N = 5 |
|---|---|---|---|
| start of the CNS decrease | | | |
| > 7 days | 0 | 0 | 3 |
| 2 - 7 days | 1 | 0 | 1 |
| ≤ 1 day | 9 | 1 | 1 |
| minimum CNS value | | | |
| > 100 AU | 1 | 0 | 4 |
| ≤ 100 AU | 9 | 1 | 1 |

DETECTION OF APOPTOTIC PRODUCTS

U.S. provisional application 60/079,494 filed Mar. 26, 1998, DE 19811739.6 filed Mar. 18, 1998 and PCT/EP99/001798 filed Mar. 18, 1999.

The present invention concerns a method for the determination of apoptotic products in patient samples in which the concentration of the apoptotic products in serum samples is correlated with the effectiveness of the tumour therapy and thus serves to monitor the progress of therapy. The serum samples are taken at various times and determined. In particular the present invention concerns a method in which the concentration of nucleosomes in serum samples of tumour patients is determined in order to determine the effectiveness of tumour therapy. In addition the use of a method for determining apoptotic products in serum samples of tumour patients to determine the effectiveness of tumour therapy is a subject matter of the present invention.

A eukaryotic cell can die in two fundamentally different ways. One way is necrosis which is cell death as a result of damage e.g. due to an inadequate blood supply and thus inadequate oxygen and nutrient supply or as a result of poisoning or physical damage (mechanical damage, frost or heat). The other path, so-called programmed cell death, is of major importance for the development and functionality of tissues, organs and organisms as a whole (J. Cohen, Advances in Immunology 50 (1991), 55 –85). Cells which die in this manner have DNA fragments associated with histones in the cytoplasm as mononucleosomes and oligonucleosomes. Such a feature is also observed in an induced cell death such as that triggered by ionizing rays (Yamada et al., Int. J. Radiat. Biol. 53 (1988), 65) or by certain monoclonal antibodies such as e.g. anti-Fas (Yonehara et al., J. Exp. Med. 169 (1989), 1747–1756) or anti-APO-1 (Trauth et al., Science 245 (1989), 301–304). Cytotoxic T cells and natural killer cells also cause such an induced cell death with the described characteristics (Sanderson, Biol. Rev. 56 (1981), 153–197, S. Curnow et al., Cancer Immunol. Immunother. 36 (1993), 149–155 and Berke, Immunol. Today 12 (1991), 396 –399). They, however, also result in an increased permeability of the plasma membrane as observed in necrosis (Krähenbühl et. al., Immunol. Today 12 (1991), 399–402). The described type of programmed or induced cell death is called apoptosis (Wyllie et al., Int. Rev. of Cytol. 68 (1980), 251–301). It is characterized by blister-like protuberances of the plasma membrane, condensation of the cytoplasm and activation of endogenous endonucleases. Thus in contrast to necrosis, apoptosis is an active process of the eukaryotic cell. It is therefore also not induced by killing the cells by heating, freezing and thawing or lysis with a lytic antibody (R. Duke et al., Proc. Natl. Acad. Sci. 80 (1983), 6361–6365). The calcium and magnesium dependent endonuclease activated in apoptosis cleaves the DNA double strand in the readily accessible linker regions between the nucleosomes into mononucleosomes and oligonucleosomes. In contrast the DNA in the nucleosomes is closely associated with the core histones H2A, H2B, H3 and H4, and therefore protected from cleavage by the endonuclease (Burgoyne et al., Biochem. J. 143 (1974), 67 and Stach et al., J. Neurochem. 33 (1979), 257). Hence after extraction of the DNA and separation in an agarose gel the DNA ladder that is typical of apoptotic cells is seen which is a pattern of DNA fragments with a length of ca. 180 base pairs or multiples thereof (Wyllie, Nature 284 (1980), 55–556 and J. Cohen, Advances in Immunology 50 (1991), 55–85). The plasma membrane of the cells remains intact in this early stage of apoptosis. Mononucleosomes and oligonucleosomes accumulate in the cytoplasm of the dying cell (Duke et al., Lymphokine Research 5 (1986), 289–299).

Apoptosis occurs during the embryonic period and during the development of the immune and nervous system for the purpose of homeostasis in order to regulate the number of cells (for example in the intestinal mucosa) and to ensure the function of cells in the organism; it also occurs in pathological processes such as inflammatory reactions, as a result of ischaemic lesions (e.g. in a cerebral insult (stroke), myocardial infarction, pulmonary embolism), in autoimmune diseases (such as systemic Lupus erythematosus (SLE)), as a defense reaction following bone marrow transplantations and transplantations of other organs (host versus graft, graft versus host reaction) (Darzynkiewicz, Cytometry, 1997, 27: 1–20, Kerr, Cancer 1994, 73: 2013–2025, Kornbluth, Immun letters 1994, 43: 125–132, K. Matsushita, Neuroscience 83 (1998), 439–448 and R. Majno and I. Joris, Am. J. Path 146 (1995), 3–15).

Apoptotic processes can be observed in patients with malignant and benign tumours (Leon, Cancer Res. 37 (1977), 646–650; Shapiro, Cancer 51 (1983), 2116–2120 and Fournie, Cancer Letters 91 (1995), 221–227). Hence in malignant tumours an increased cell turnover is often observed i.e. the cell proliferation rate as well as the cell death rate is increased (Kerr, Cancer 73 (1994), 2013–2025 and Cotter, Anticancer Research 10 (1990), 1153–1160). The latter is an expression of massive apoptotic cell extinction. Controlled, programmed degradation of DNA, cell nucleus and organelles, packaging of the cell contents into apoptotic bodies as well as phagocytosis by macrophages and neighbouring cells ensure complete recycling without remnants (Darzynkiewicz, Cytometry 27 (1997), 1–20, Kerr, Cancer 73 (1994), 2013–2025 and Cotter, Anticancer Research 10 (1990), 1153–1160). If this disposal system is overloaded, cellular components among others also reach the blood circulation (Emlen, J. Immunol 152 (1994), 3685–3692, Kornbluth, Immun Letters 13 (1994), 125–132, Emlen, J. Immunol. 148 (1992), 3042 and Franek, FEBS Letters 284 (1991), 285–287). Thus higher DNA concentrations were found in the serum and plasma of patients with malignant tumours (Leon, Cancer Res. 37 (1977), 646–650 and Shapiro, Cancer 51 (1983), 2116–2120 and Fournie, Cancer Letters 91 (1995), 221–227) the DNA being mainly present in the circulation bound to histones in the form of mononucleosomes and oligo-nucleosomes (Rumore, J. Clin. Invest 86 (1990), 69–74 and Burlingame, J, Immunol 156 (1996), 4783–4788). Nucleosomes can be detected by several methods, e.g. as described in U.S. Pat. No. 5,637,465.

The absolute amount of apoptotic products, such as nucleosomes, in the serum can be correlated with the extent of the malignant disease. There is sometimes a considerably higher concentration of serum nucleosomes in advanced diseases. Furthermore it is known that apoptosis is induced by radiotherapy, hyperthermia, hormone ablation and by various cytostatic drugs (Kerr, Cancer 73 (1994), 2013–2025 and Sakakura, Br. J. Cancer 77 (1998), 159–166).

WO93/09437 describes a method for detecting and quantitating soluble nuclear matrix proteins in body fluids and extracellular media. This method is described as being useful for monitoring the viability of cells and tissue, for evaluating the progress of a disease or its treatment, and for evaluating the cytotoxicity of unknown compounds.

WO96/40985 discloses a method for quantitatively measuring apoptosis by determining the E(γ-glutamyl) lysine isodipeptide concentration. The before mentioned methods are not well-suited as a fast marker for the effectiveness of the therapy of patients in which apoptosis is induced as a result of disease or therapy. Moreover, the described methods are not convenient for the daily use in a clinical environment.

Surprisingly it was found that the change in the concentration of apoptotic products in samples taken from patients correlates with the effectiveness of the therapy, whereby these are patients in which apoptosis is induced as a result of disease or therapy. These are tumour patients or patients that have been subjected to a chemotherapy or radiotherapy treatment or patients with acute inflammatory processes during antibiotic treatment. This means that the progress of therapy can be monitored by measuring the concentration of apoptotic products in samples taken from the previously mentioned patients.

In particular it was found that the concentration of apoptotic products in the serum of tumour patients during radiotherapy or chemotherapy can be used as a marker for the effectiveness of the treatment.

Thus a subject matter of the present invent on is a method for the determination of apoptotic products in samples taken from patients, these being patients in which apoptosis is induced as a result of disease or therapy characterized in that the concentration of the apoptotic products in suitable patient samples is correlated with the effectiveness of the therapy and thus serve as a follow-up of the therapy.

In particular a subject matter of the present invention is a method for the determination of apoptotic products in samples taken from patients, these being tumour patients or patients that are subjected to chemotherapy or radiotherapy or patients with acute inflammatory processes during antibiotic treatment which is characterized in that the concentration of apoptotic products in suitable patient samples is correlated with the effectiveness of the therapy and thus serve as a follow-up of the therapy.

Suitable patient samples in the sense of the present invention are: serum, plasma, liquor, sputum (bronchial secretion), ascites (peritoneal fluid), the material from the puncture of the pleural cavity, synovia (synovial fluid) and urine. Serum samples are preferably used for the method according to the invention especially when determining the effectiveness of a tumour therapy.

The effectiveness of tumour therapy can be determined by means of the remission rate on the basis of image generating processes (X-ray, computer tomography). By definition a complete remission is understood as the complete disappearance of the tumour for at least eight weeks and partial remission means a regression of the tumour manifestations by more than 50% with regard to their volume; no change reflects the state between a 50% decrease and a 25% increase of the tumour mass; progression denotes a progression of more than 25% (UICC criteria).

The patient samples, for example serum samples, are taken at various times and determined.

Apoptotic products whose concentration can be measured are for example nucleosomes or products of caspases (e.g. fragments of cytokeratins), APO-I (fas), APO-2, APO-3, Bcl-2, blk, caspases, fas-receptor fragments, fos, FLICE enzymes, mdm-2, TNF-α, TNF receptor fragments but also further substances involved in the apoptotic process come into consideration as the analyte.

The present invention in particular concerns a method for the determination of the concentration of apoptotic products, in particular of nucleosomes in suitable patient samples of tumour patients in which the effectiveness of the therapy is correlated with the concentration of the apoptotic products in these patient samples in particular the concentration of nucleosomes.

A method for determining the concentration of nucleosomes in serum samples of tumour patients is particularly preferred in which
 a) the serum of a tumour patient is incubated with an anti-histone antibody and with an anti-DNA antibody in which one of the antibodies is bound to a solid phase before, during or after this incubation and the other antibody is a labelled antibody
 b) the solid and liquid phase are separated and
 c) the label is determined in one of the two phases in order to determine the concentration of nucleosomes in serum samples of tumour patients. The commercially available Cell Death Detection$^{plus}$ ELISA from Boehringer Mannheim GmbH, Germany is for example suitable for determining the concentration of nucleosomes in serum samples of tumour patients.

Some modifications are made for an application in liquid media in order to quantitatively determine the concentration of nucleosomes:

Among others a standard curve using highly apoptotic material is used as a basis for the interpretation instead of an concentration factor (CF) related to a negative control: The standard material is for example obtained by incubating whole blood from several (healthy) blood donors.

A further subject matter of the invention is the use of a method for the determination of apoptotic products in serum samples of tumour patients to determine the effectiveness of tumour therapy. The use of the Cell Death Detection$^{Plus}$ ELISA kit from Boehringer Mannheim is particularly preferred for determining apoptotic products in blood samples of tumour patients.

In particular the nucleosome concentration in the serum was observed during radiotherapeutic or chemotherapeutic treatment of patients with a malignant tumour disease and correlated with the clinical course and tumour markers. The nucleosome concentration in the serum was for example determined before the therapy and at certain time intervals during and after the end of the respective therapy. Concentrations of nucleosomes that were increased to different extents occurred in the serum very rapidly after the start of the therapy which were observed during the course of the therapy and appeared to give an early indication of the therapy efficiency in particular for radiation.

The maximum occurrence of apoptosis during chemotherapy can be expected about 24 to 48 hours after starting the administration of drugs, depending on the selected cytostatic agents and dosage (Meyn, Cancer Chemother. Pharmakol. 33 (1994), 410–414) and nucleosomes appear in the circulating blood with a slight time delay relative to the apoptosis.

The therapy was carried out in cycles the length of which varied between 1 and 5 days depending on the protocol and which were interrupted by breaks of several weeks (usually 3 to 4 weeks). In order to determine the kinetics of the nucleosome concentration in the serum, blood samples were for example taken before the start of the first cycle, on the second and fourth day of the cycle, in each case before administration of the cytostatic agent. This procedure was repeated for each new cycle. The initial value before starting therapy, the increase of the nucleosome concentration in the serum, the maximum value reached during therapy, the decrease in the nucleosome concentration and the minimum value between the cycles as well as the kinetics of the nucleosome basal concentrations which in each case were determined before the start of a new cycle were correlated with the clinical course.

In many patients there was an increase in the nucleosome concentration after three to four days, and subsequently a slow decrease. When the cycle was repeated an increase was found again which in many cases was less pronounced. There was a correlation between the clinical course and kinetics of the basal nucleosome concentration that was determined before each new cycle. Patients with a regression of the tumour disease mainly had a decrease in the basal nucleosome concentration. An increase in the basal nucleosome concentration was mainly observed in patients with a progression of the disease (see example).

During radiotherapy the maximum occurrence of apoptosis can be expected about 4 hours after starting treatment, followed by a slow decrease of the incidence of apoptosis (Mirkovic, Radiother. Oncol. 33 (1994), 11–16); the release of nucleosomes into the circulation is expected after a brief latency period.

The treatment is carried out daily, 5 days per week over a period of 4 to 6 weeks according to the corresponding guidelines for tumour disease. Blood samples were for example taken before the first fraction, 3 hours, 6 hours, 1 day (i.e. before the second fraction), 4 days, 7 days and weekly after beginning treatment. The initial value before starting treatment, the increase in the concentration of the nucleosomes in serum, the maximum value achieved during treatment, the delay in the decrease of the nucleosome concentration and the minimum value reached during or at the end of treatment were correlated with the clinical course.

In most patients there was a rapid increase in the nucleosome concentration to different extents already 6 to 24 hours after the first radiation fraction which may depend on the type of tumour and the pre-therapeutic initial value. Furthermore the nucleosome concentration decreased after latency periods of different lengths to minimum values of different magnitudes in which an early decrease and low minimum concentration values can be correlated with a regression of the tumour (see example).

The invention in addition concerns a method in which the nucleosome concentration in the serum or in other patient samples is correlated with the response to therapy in patients undergoing a hyperthermia treatment or in which the nucleosome concentration in the serum or other patient samples is correlated with the defense reactions of the immune system in patients which have been subjected to bone marrow transplantation; a massive induction of cell death would be expected in both types of treatment. Also in the case of systemic tumour diseases and above all the various forms of leukaemia and lymphoma, the determination of the nucleosome concentration in the serum enables early and reliable information to be obtained on the efficiency of therapy and assessment of the prognosis.

Furthermore the determination of nucleosomes in the serum of patients after an acute ischaemic event such as after myocardial infarction or cerebral infarction enables an early estimation of the extent of damage. Furthermore, the test can be used for follow up and to assess the prognosis. Even in patients with acute inflammatory processes or with autoimmune diseases—above all in SLE, a disease in which the occurrence of nucleosomes and anti-nucleosome antibodies in the serum is of pathogenetic importance—the intensity and kinetics of the pathological process can be detected with this parameter.

The determination of the nucleosome concentration in other body fluids can be used to assess the extent and progress of local processes: for example in cerebrospinal fluid of patients with brain tumours, with inflammatory diseases, with cerebral hemorrhage, with degenerative diseases, after cerebral traumas and after cerebral ischaemic insults (stroke).

In ascites early diagnostic or prognostic information is conceivable in the case of a peritoneal dissemination of a malignant tumour and in the material of a puncture of the pleural cavity, in the case of a malignant pleural effusion.

In addition an early detection in the urine of a tumorous or inflammatory process in the kidney and in the efferent urinary tracts may be possible as well as in the sputum (bronchial secretion) in malignant processes of the lung.

EXAMPLE 1

Cell Death Detection$^{Plus}$ ELISA

Test principle

The Cell Death Detection$^{Plus}$ ELISA (Boehringer Mannheim, Cat. No. 1 774 425) is based on the quantitative sandwich enzyme immunoassay principle. Two monoclonal mouse antibodies are used which are directed against DNA and histones. The test can be carried out with cytoplasmic lysates, culture supernatants, plasma, serum and other body fluids and allows a specific detection of mononucleosomes and oligonucleosomes. The description given here applies to measurements in liquid media:

Test procedure

A 20 µl aliquot of the material to be tested is pipetted into a well of a streptavidin-coated microtitre plate (MTP). 80 µl of an immunoreagent composed of biotinylated anti-histone antibodies, peroxidase-labelled anti-DNA antibodies and incubation buffer (1% BSA, 0.5% Tween, 1 mM EDTA in PBS) is added, covered with an adhesive foil and incubated for 2 hours on a MTP shaker (500 rpm). During this incubation period the anti-histone antibody reacts with the histone component of the nucleosomes and immobilizes the complex via the biotin on the streptavidin-coated microtitre plate. In addition the anti-DNA antibody binds to the DNA component of the nucleosomes. In this process ds as well as ss DNA is recognized. After removing the antibody that is still unbound by washing three times with 300–400 µl incubation buffer in each case, the immobilized complexes are incubated with 100 µl ABTS (2,2'-azino-di(3-ethylbenzthiazoline sulfonate), the MTP is sealed with an adhesive foil and shaken at 250 rpm. The substrate reacts with the peroxidase label of the anti-DNA antibody and causes a colour change that is proportional to these antibodies. After an adequate colour development period it is photometrically quantified at d=405 nm against the substrate solution as a blank (reference wavelength d=492 nm).

EXAMPLE 2

Modification and standardization

Standard material

A standard curve with highly apoptotic material is used as a basis for interpretation instead of an enrichment factor:

Apoptosis is induced by incubating EDTA whole blood of three healthy blood donors for 24 hours. After centrifugation the plasma is lyophilized and stored at 4° C. When resuspended at various times reproducible maximum values in the upper measuring range of the photometer are obtained with an optical density (OD) of 2500 mA; there is a good long-term stability as well as a linear dilution behaviour in the entire range from 0 to 2500 mA. Hence comparability is ensured within a test as well as between several test runs.

A 1:24 dilution of the standard material with incubation buffer is used as the highest standard value which reaches 2500 mA after 30 min. The other dilution steps (1:24, 1:32, 1:48, 1:64, 1:96, blank) yield a linear dilution curve which corresponds to a straight line through the origin (FIG. 1).

The ELISA can already detect a nucleosome content of $10^3$ cells.

Measuring Time

In order not to exceed an acceptable measurement inaccuracy limit of 5% due to delays that result from pipetting steps, the ABTS incubation period is set at 30 minutes.

Measuring unit

Nucleosomes possibly differ in their accessibility for antibody binding depending on the form in which they are present: as mononucleosomes or oligonucleosomes, the latter with or without a tertiary structure. Hence the amount of bound and POD-labelled anti-DNA antibody does not necessarily correspond to the exact nucleosome concentration in the sample material.

Therefore absolute concentration data are not used and a scale of so-called AUs (arbitrary units) is introduced. 1000 AU equates with the highest standard level (2500 mA after 30 min); the scale is linear. This therefore takes into account the lack of knowledge about the ratio of mononucleosomes to oligonucleosomes and the resulting variability concerning the amount of binding sites of the antibodies while at the same time increasing the comparability between the tests.

EXAMPLE 3

Preanalytical Standardization

Matrix

In the present experiments serum is used as a matrix. Haemolysis can lead to false positive test results; the centrifugation is therefore carried out for 15 min at 3000 rpm within a period of 2 hours after collection.

Sample Stabilization

The addition of 1/10 parts by volume 100 mM EDTA (TRIS buffer, pH 8) directly after the removal of the serum inhibits $Ca^{2+}$ and $Mg^{2+}$-dependent endonucleases e.g. DNase I and endonucleases that are active in an acid range such as DNase II with an activity optimum at pH 4.5. This prevents a potential cleavage of recognition sites of the anti-DNA antibodies and prevents a decrease of the measured values.

Test Preparation

After thawing attention must be paid to adjustment to room temperature and careful homogenization of the sample material. The serum samples are diluted 1:4 with incubation buffer (20 µl serum, 60 µl incubation buffer) and subsequently used in the test.

In comparison with the standard curve, a linear dilution line is observed for dilutions of the serum (FIG. 1).

EXAMPLE 4

Description of the Patient Group

Sera from a total of 507 test persons were analysed. 445 of these were sera from patients which were under treatment in the period from August 1996 to December 1997 and 62 were from healthy persons.

Healthy persons

Sera from 62 healthy test persons were tested. The age distribution of the persons extended from 20 to 60 years with an average of 35 years; 33 women (53%) and 29 men (47%) took part in the study.

Patients with Benign Diseases 108 sera from patients with benign diseases were examined: 39 had benign gastro-intestinal diseases (mainly colitis, pancreatitis, cholecystolithiasis, subileus of various causes), 13 had benign pulmonary diseases (above all emphysema, pneumonia), 37 had benign gynaecological diseases (above all ovarian cysts, endometriosis, uterus myomatosus), 19** had other benign diseases (above all abscesses, nodular goitre, CHD).

50 of the 108 patients suffered from acute inflammatory diseases which were divided into 5 different categories (10 in each) based on the levels of C-reactive protein:

(I:CRP$\leq$1 ng/mL, II:1 ng/mL <CRP$\leq$5 ng/mL, III:5 ng/mL <CRP $\leq$10 ng/mL; IV: 10 ng/mL <CRP $\leq$20 ng/mL, V:20 ng/mL <CRP).

Patients with Solid Tumours

In addition sera from 337 patients with solid tumours (CA=carcinoma) were examined; these were subdivided into 38 bronchial CAs, 60 colon CAs, 44 other gastrointestinal CAs, 58 mammary CAs, 43 ovarian CAs, 19 other gynaecological CAs, 8 ENT CAs, 16 lymphomas, 20 kidney CAs, 17 prostate CAs and 14 other CAs.

Blood samples were withdrawn in each case before the operative primary therapy or before chemotherapy or radiotherapy in order to measure the spontaneous, pre-therapeutic cell death rate by means of the nucleosome determination.

Follow-Up Observation

Of these 337 patients, an additional follow-up monitoring was carried out in 16 patients during primary or secondary radiotherapy (6 with bronchial CA, 4 with lymphomas, 4 with ENT CA, 2 with colon CA) and in 20 patients under chemotherapy (7 with lymphomas, 6 with colon CA, 2 with pancreatic CA, 2 with bronchial CA, 2 with sarcomas, 1 with ENT CA).

In the patients treated with radiation, blood samples were taken before radiation and 3, 6, 24 and 72 hours, and one week after the start of radiation and in addition before the start of each respective first weekly radiation unit. Since the therapeutic plan of most patients included a daily irradiation it must be taken into account that after the fourth measurement a new therapy unit took place.

The nucleosome content was measured in patients under chemotherapy before therapy and on the second and fourth day and one week after administration of the first dose and in addition weekly or before the start of the next treatment cycle.

EXAMPLE 5

Method Results

Matrix

We tested in parallel the serum and plasma from 10 test persons, of these 4 were healthy, 4 were tumour patients and 2 were patients with acute inflammatory diseases. In this case the nucleosome concentrations in the serum were usually found to be higher than in the plasma (N=9). In one patient with extremely high CRP values above 45 ng/ml the measured results were equally high in the serum and the plasma.

Stability

Figure 2:
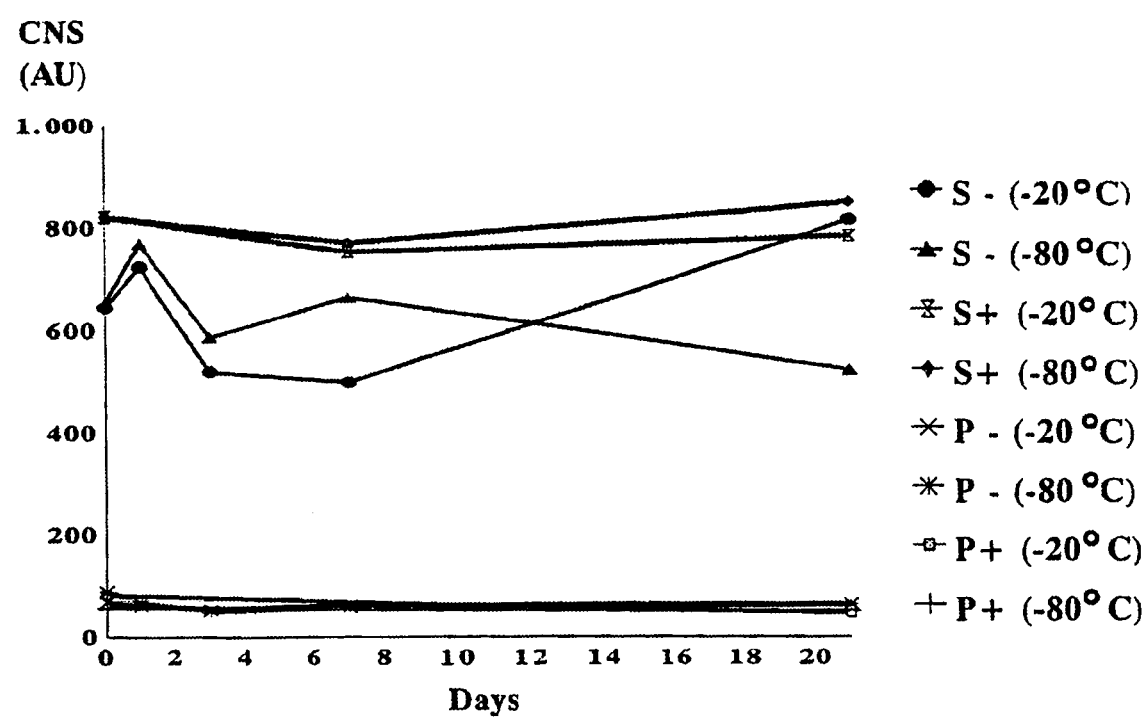

These serum and plasma samples were stored for a period of three weeks at 25° C., 4° C., −20° C. and −80° C. with and without the addition of 10 mM EDTA (pH 8). The best stability was observed in serum to which 10 mM EDTA (pH 8) (see above) was added immediately after centrifugation and which was stored at a temperature of −20° C. or −80° C. (FIG. 2).

Pre-Analytics

Influence of Haemolysis

Figure 3:
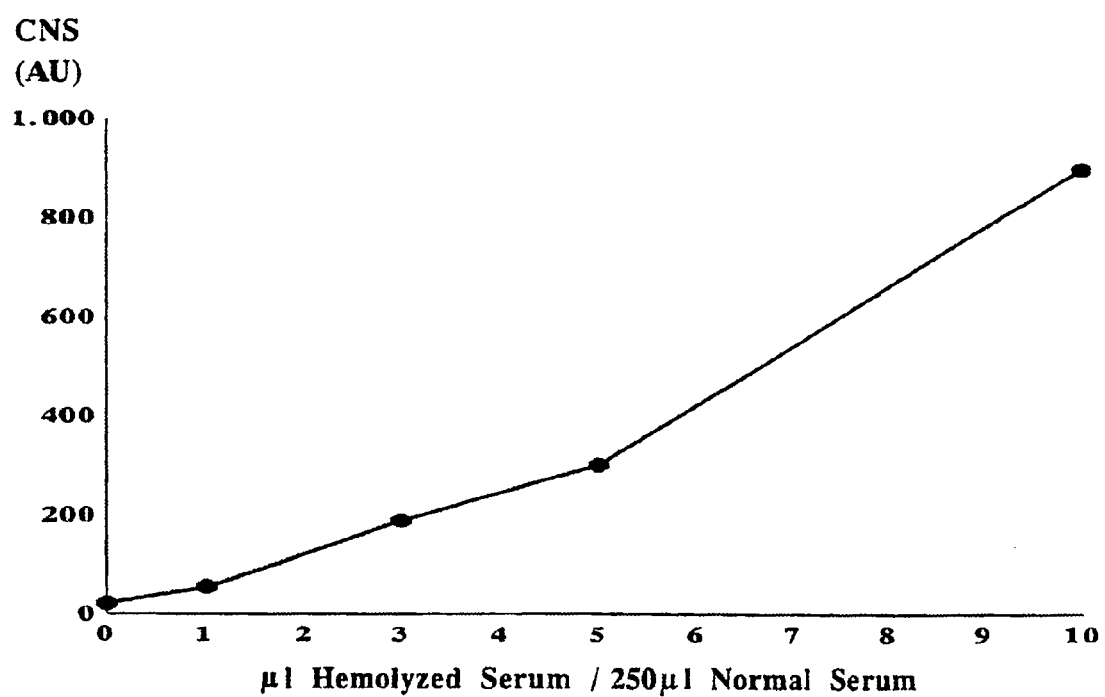

Slight haemolysis was induced in a whole blood sample by smoothly shaking and exposure to heat (37° C.) for 4 hours. After removing the serum it was used to titrate a healthy low apoptosic serum. The measured signal increased continuously with an increasing amount of haemolysate (FIG. 3).

Influence of the Time of Centrifugation

After blood withdrawal whole blood samples were stored for 0, 2, 4 and 6 hours before centrifugation under various storage conditions (37° C., 25° C., 4° C.). Afterwards EDTA (see above) was added to them or they were frozen untreated. The longer the time period before EDTA addition, the higher were the measured values in the serum. This effect became more pronounced on storage at higher temperatures (37° C.).

Influence of the Time of EDTA Addition

After centrifugation sera were stored at 37° C., 25° C. and 4° C. before adding 10 mM EDTA (pH 8) after 0, 2, 4, 6 or 8 hours and afterwards they were immediately frozen at −20° C. The later the EDTA was added to the serum the lower were the signals obtained in the serum. Exceptions were very low values or values above the measuring range which remained constant. The temperature did not have a significant influence.

Influence of the Time of Freezing

Figure 4:
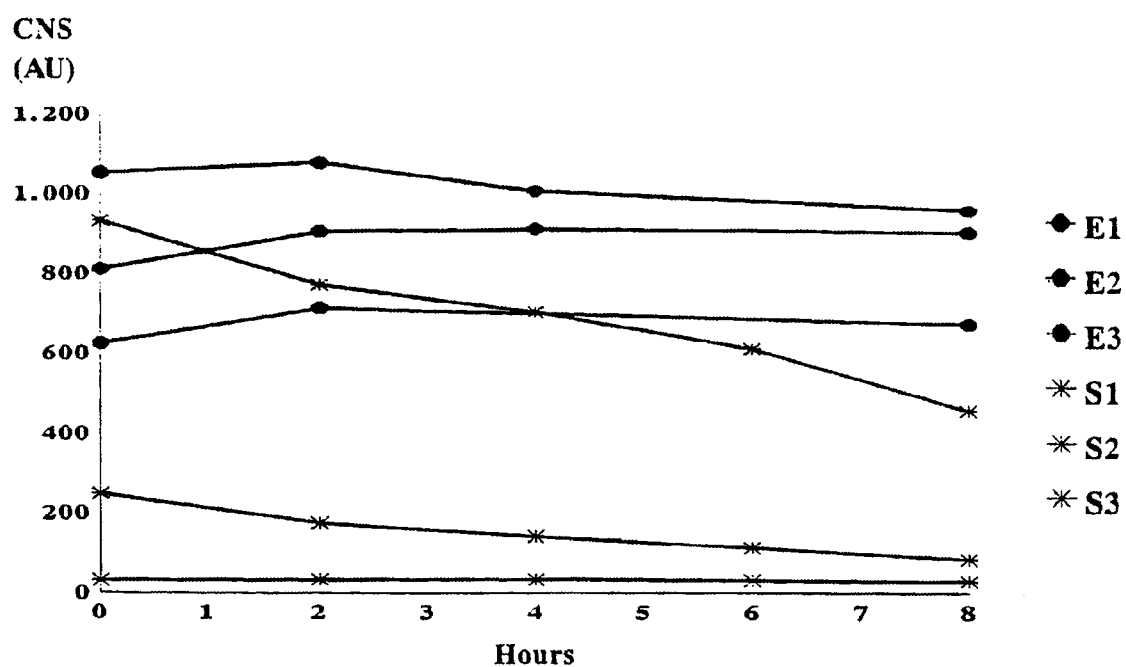

Sera were stored for 0, 2, 4 and 6 hours at 37° C., 25° C. and 4° C. after centrifugation and immediate addition of 10 mM EDTA before they were deep-frozen at −20° C. Neither time nor temperature had an influence on the measured signals obtained (FIG. 4).

Long-Term Stability of the Sample Material

Figure 5:
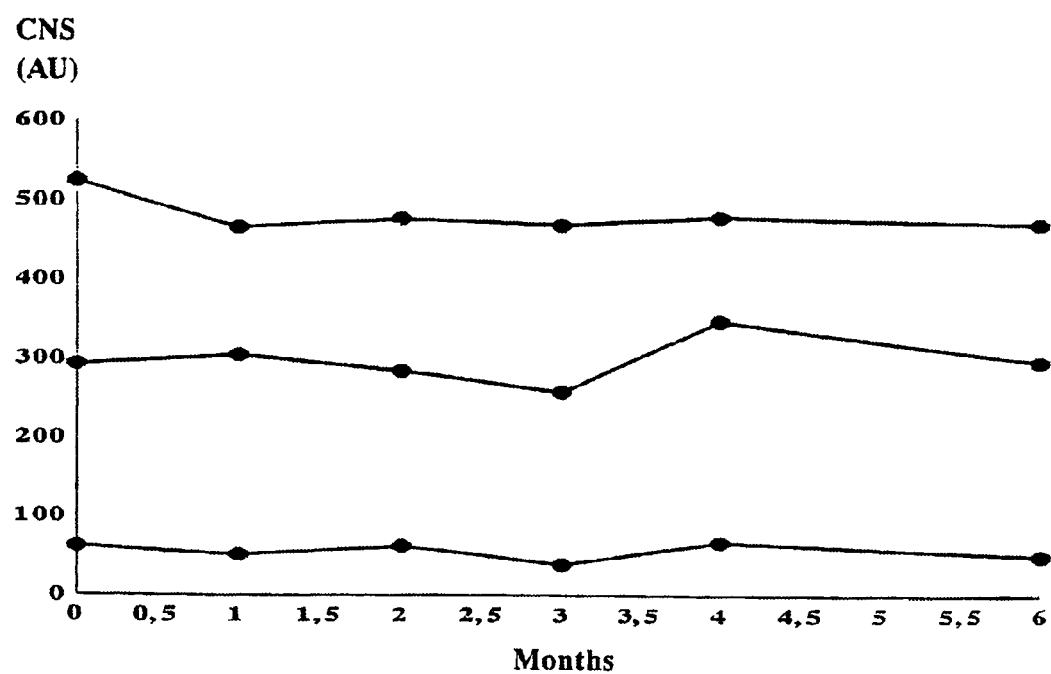

The long-term stability was checked after 1, 2, 3, 4 and 6 months with three sera frozen at −20° C. ($x_1$–$x_3$) with low ($x_1$ =55 AU), medium ($x_2$=297 AU) and high ($x_3$=481 AU) test results. Stable measured signals were obtained for all three sera with a CV of 4.2%–9.2% (FIG. 5).

Quality Criteria of the Test

Imprecision

In order to assess the imprecision of the measurement the coefficients of variation of different serum pools ($x_1$–$x_4$) were determined. Depending on the measurement values the interassay CV (n=14) varied between 8.6% ($x_1$=455 AU) and 13.5% ($x_2$=235 AU), the intra-assay CV (n=10) varied between 3.0 ($x_3$=327 AU) and 4.1% ($x_4$=181 AU), sera with higher measurement values having a lower imprecision.

Analytical Specificity

A measurement signal is linked to the complex formation of biotinylated anti-histone antibodies, nucleosomes and peroxidase-labelled DNA antibodies: non-biotinylated anti-histone antibodies were added by titration to the standard immuno-reagent containing biotinylated anti-histone antibodies which was incubated with a highly apoptotic serum. The measured signals decreased rapidly as the concentration of the non-biotinylated anti-histone antibodies increased which corresponds to a competitive displacement competition between the anti-histone antibodies provided with or without biotin and asymptotically approximated the region of healthy persons.

Figure 6:
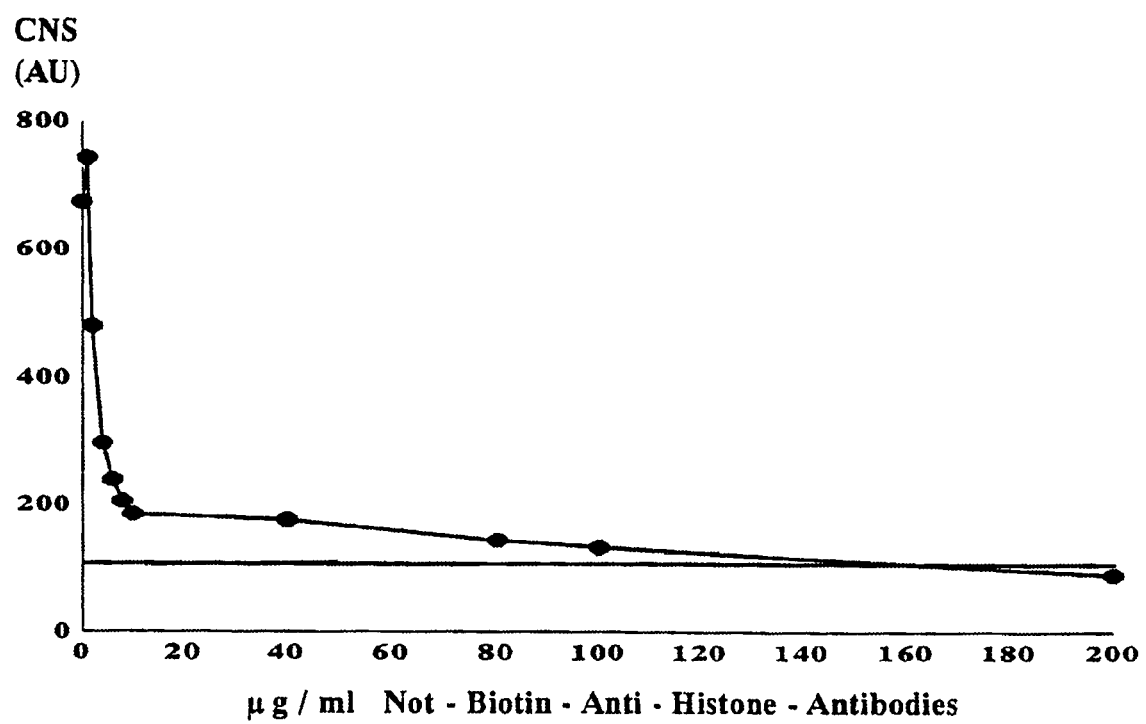

Hence nucleosomes, free DNA, histones, anti-histone or anti-DNA antibodies alone cannot cause interfering changes of the OD (FIG. 6).

Lowest Detection Dose (LDD)

The lowest detectable concentration was calculated from the mean value of the blank (n=20)+3x standard deviation as 16 AU.

Test Modifications

Standard Curve and Measuring Unit

By establishing a standard curve as described above it was possible to achieve an interassay imprecision of less than 10%.

In addition measurement in AU (arbitrary units) compared to mU optical density enabled the interassay imprecision (N=14) to be increased from 15.3% to 8.6% ($x_1$=455 AU=1007 mU) and from 17.0% to 13.5% ($x_2$=235 AU=437 mU) whereas the intraassay imprecision (N=10) was constant: 3.0% or 3.3% ($x_3$=327 AU=882 mU) and 4.1% or 4.0% ($x_4$=181 AU=480 mU).

EXAMPLE 6

Clinical results

Measurement Results and Distribution of Values

Healthy Test Persons

Nucleosome concentrations below 100 AU were measured in the serum of 60 out of 62 (=96.8%) healthy test persons. Only 2 (=3.2%) had nucleosome concentrations between 100 and 200 AU. The median was at 24 AU, the mean was 34 AU. No differences were found with regard to age, sex or habits (e.g. smoking, alcohol) of the test persons.

Patients with Benign Diseases

In the case of patients with benign diseases (N=108) a nucleosome concentration in the serum above 100 AU was found in 59.3% of the cases and it was above 500 AU in 17.6%; the median was 147 AU, the mean was 271 AU.

Classified according to organ systems 61.5% were above 100 AU and 15.4% were above 500 AU for benign pulmonary diseases, 48.7% were above 100 AU and 23.1% were above 500 AU for benign gastrointestinal diseases, 67.6% were above 100 AU and 10.8% were above 500 AU for benign gynaecological diseases and 63.2% were above 100 AU and 21.1% were above 500 AU for all other benign diseases.

Of these benign diseases, 50 were selected with acute inflammatory diseases and a known CRP: in patients from group 1 (CRP ≦1 ng/ml) (N=10) the nucleosome concentration in the serum was above 100 AU in 40% and above 500 AU in 10%, in patients from group 2 (1 ng/ml <CRP ≦5 ng/ml) (N=10) it was above 100 AU in 50% and above 500 AU in 20%, in patients from group 3 (5 ng/ml <CRP ≦10 ng/ml) (N=10) is was above 100 AU in 80% and above 500 AU in 30%, in patients from group 4 (10 ng/ml <CRP <20 ng/ml) (N=10) it was above 100 AU in 80% and above 500 AU in 30%, in patients from group 5 (CRP >20 ng/ml) (N=10) it was above 100 AU in 80% and above 500 AU in 60%. This demonstrates the tendency towards higher nucleosome concentrations in the serum from patients with higher CRP values.

Patients with Solid Tumours

In patients with various solid tumours a very broad range of values was found independent of the location. In 63.2% of patients the serum nucleosome concentration was over 100 AU and in 24.6% was over 500 AU. The median was calculated as 183 AU, the mean as 329 AU.

Nucleosome concentrations in the serum of more than 100 AU were in particular measured in 92.1% of patients with bronchial CA, in 58.3% of patients with colon CA, in 54.5% of patients with other gastrointestinal CAs, in 75.9% of female patients with mammary CA, in 72.1% of female patients with ovarian CA, in 68.4% of female patients with other gynaecological CAs, in 75.0% of patients with ENT CA, in 56.3% of patients with lymphomas, in 40.0% of patients with kidney CA, in only 5.9% of patients with prostate CA and in 50.0% of patients with other CAs.

Figure 7A:
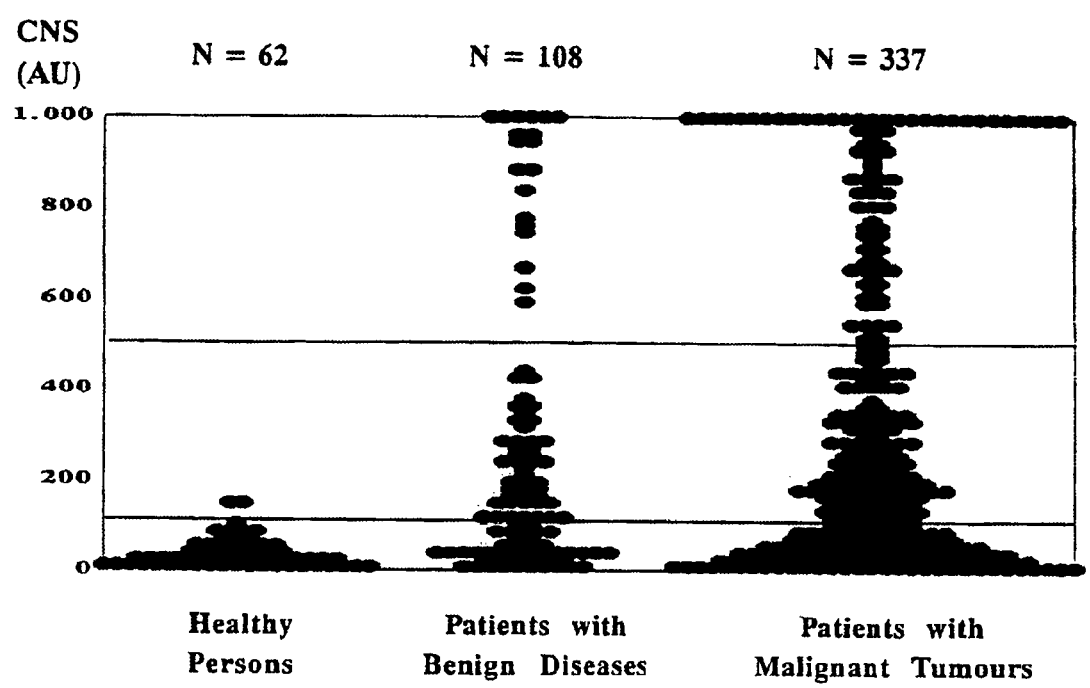

We found nucleosome concentrations above 500 AU in 36.8% of patients with bronchial CA, in 21.7% of patients with colon Ca, in 22.7% of patients with other gastrointestinal CAs, 25.9% of female patients with mammary CA, in 34.9% of female patients with ovarian CA, in 21.1% of female patients with other gynaecological CAs, in 12.5% of patients with ENT CA, in 37.5% of patients with lymphomas, in 15.0% of patients with kidney CA, in 0% of patients with prostate CA as well as in 14.3% of patients with other CAs (FIG. 7a, b, c and FIG. 13).

Follow-Up Observations

The nucleosome concentration in the serum was monitored during follow-up in patients with inflammatory diseases as well as in patients during radiotherapy and chemotherapy in order to make a comparison between the development of the nucleosome concentration in the serum and the clinical findings and response to therapy.

Figure 8:
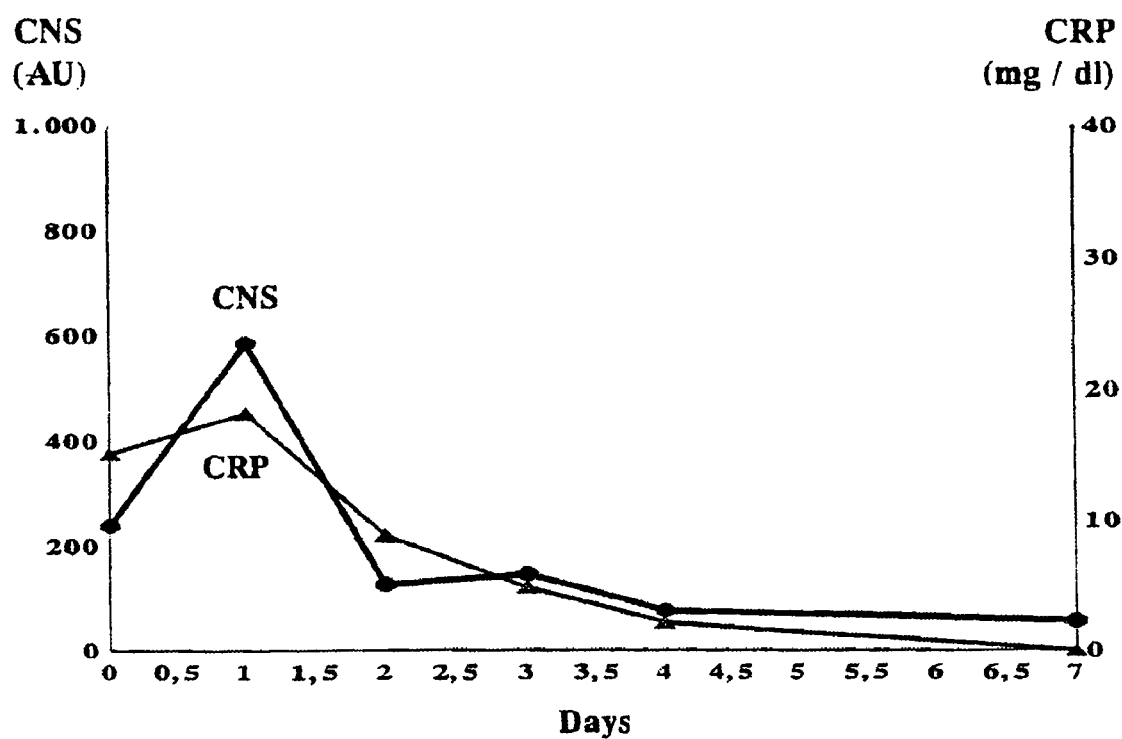

In the case of patients with inflammatory diseases the nucleosome concentration in the serum correlated with the CRP and the clinical findings (can be objectivized e.g. by sonography) i.e. a high nucleosome concentration in the serum and a high CRP was found in the acute stage of the disease and both values decreased in parallel when the clinical condition improved (FIG. 8).

Figure 9:
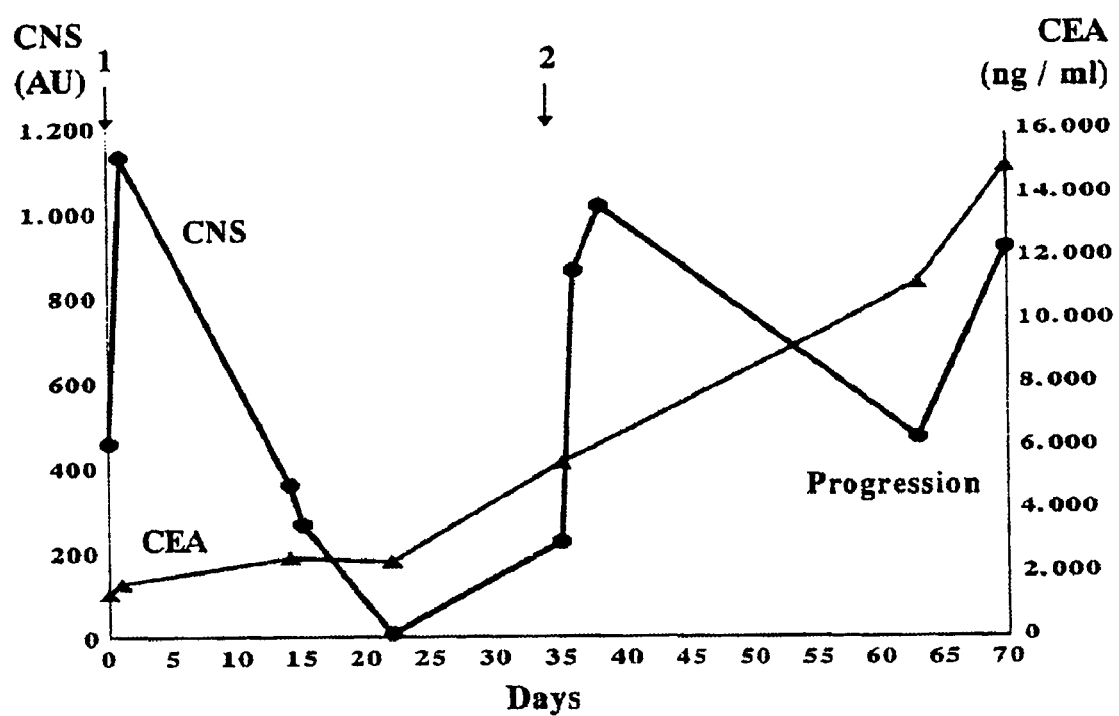

The course in patients under chemotherapy can only be assessed individually and with knowledge of the clinical backgrounds. Characteristic for most of the observed patients was a steep increase of the nucleosome concentration in the serum with a different drug-dependent latency (24–72 hours) after the start of therapy. In the further course the values often decreased again. Infections or other side effects caused among others a temporary increase of the nucleosome concentration and complicated the assessment of progress (FIG. 9).

Neither the pre-therapeutic value, the rate of increase nor the maximal level of increase correlated with the therapeutic response. There was regularly a decrease of the nucleosome concentration between the cycles independent of the further course of the disease. Finally a comparison of the basal nucleosome values is suitable as a criterium for assessing the course of therapy which were measured in each case at the beginning of a new therapy cycle: In all 8 patients with a partial or complete remission a decrease of the basal nucleosome concentration was observed whereas an increase was only seen in patients with a progression of the disease (FIG. 14).

Figure 10:
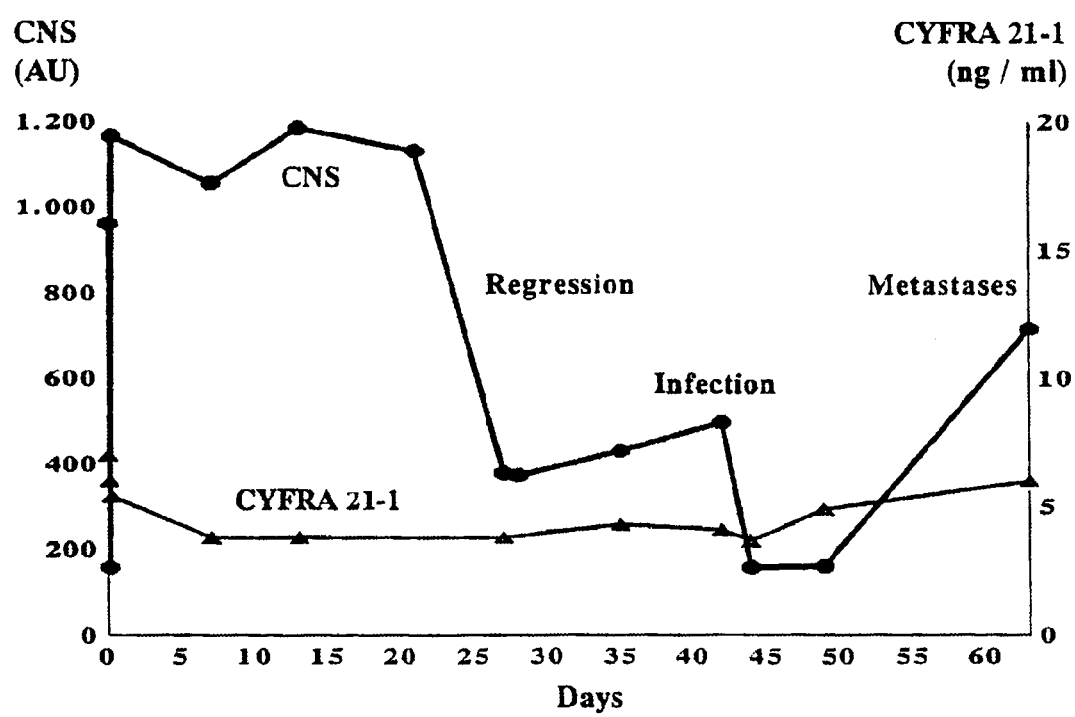

In patients under radiotherapy: there was usually a rapid increase in the serum nucleosome concentration at the beginning of radiotherapy due to massive apoptosis induction. The latency period of 6–24 hours was shorter than with chemotherapy. Furthermore in some patients an intermediate decrease in the nucleosome concentration in the serum was apparent after 3 or 6 hours before it subsequently rapidly increased. In the followup—sometimes after persistently high values—a decrease was observed in many cases which was often associated with a regression of the tumour which could be confirmed later by imaging methods (FIG. 10).

There was a correlation of the pre-therapeutic nucleosome concentration and the maximum nucleosome concentration during radiotherapy: 7 of 16 patients had similarly high pre-therapeutic and maximum values above 500 AU, 5 of 16 each had similarly low values below 100 AU, 4 of 16 exhibited a strong increase from considerably below 500 AU to considerably above 500 AU. Neither the pre-therapeutic nucleosome concentration nor the maximum nucleosome concentration during radiotherapy correlated with the response to therapy (remission of the tumour.

In 9 of 10 patients with a partial or complete remission, it was possible to observe the start of a decrease in the nucleosome concentration in the serum within 24 hours after reaching the maximum value.

In contrast, in 3 of 5 patients in whom a progression of the disease was observed, the decrease of the nucleosome concentration in the serum started more than 7 days after reaching the maximum value, in one of the 5 patients it was between 2 and 7 days and in one patient within 24 hours. One patient with no change of disease stagnated also exhibited the start of a decrease in the nucleosome concentration within less than 24 hours.

In addition the response to therapy correlated with the final value of the decrease of the nucleosome concentration in the serum: In 9 of 10 patients with complete or partial tumour remission the minimum values were below 100 AU, whereas they were above 100 AU in 4 of 5 patients with progression. The patient with no change of disease under therapy had a minimum value below 100 AU (FIG. 15).

Further Examples of Other Diseases

Figure 11:
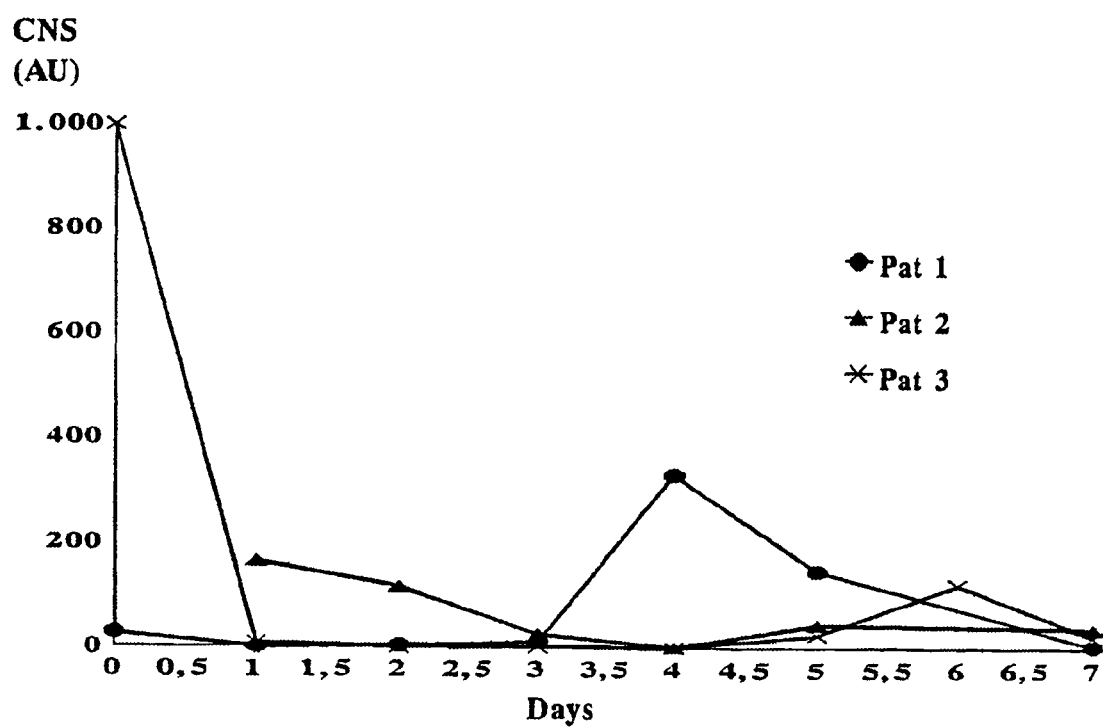

In patients with cerebral infarction (stroke), blood was collected immediately after admission into the hospital (up to 6 hours after the event) and at daily intervals and the concentration of nucleosomes in the serum was determined. The 3 examined persons had different values immediately after infarction which decreased into the range of healthy persons after one to three days. In one patient there was a temporary increase in the serum nucleosome values (FIG. 11).

In one patient with cerebral lymphoma the nucleosome concentration in the liquor was examined. The liquor was withdrawn from the spine to relieve intermittent excessive liquor pressure which was accompanied by a deterioration of the clinical state of the patient and admixed with 10 mM EDTA corresponding to the treatment of serum.

Figure 12:
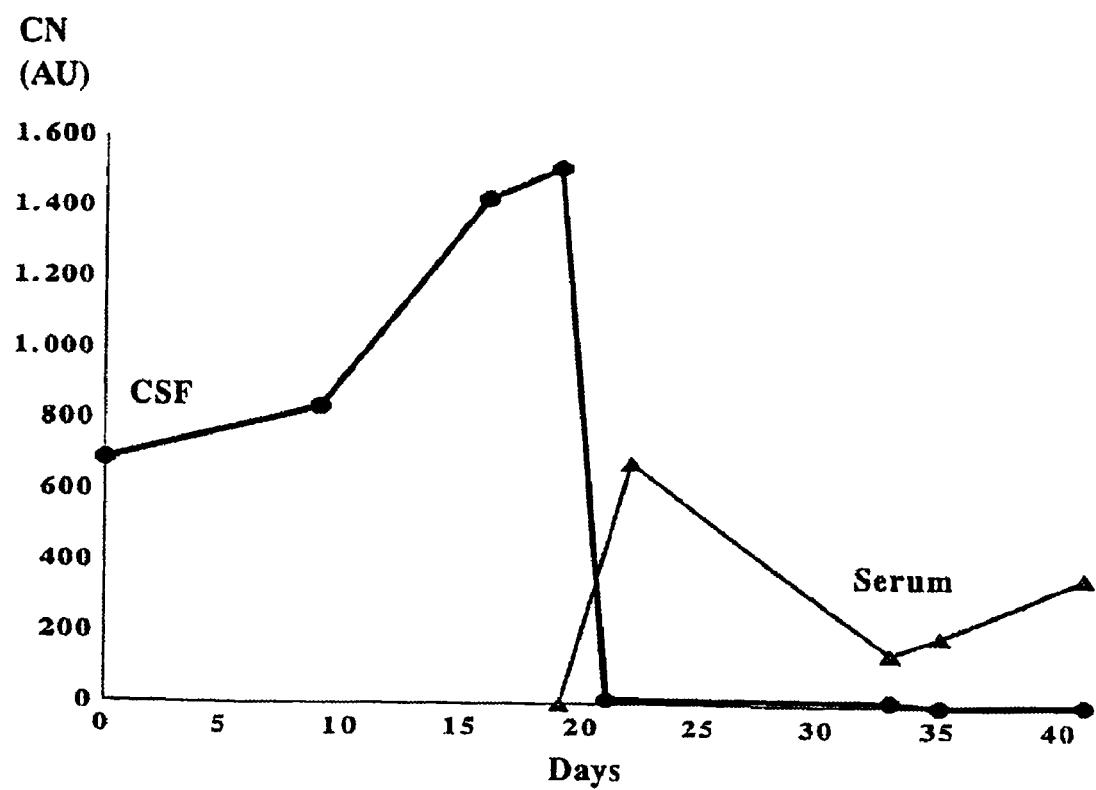

Nucleosomes were also found in measurable concentrations in the liquor and an increase in the liquor nucleosome values was accompanied by a clinical deterioration, whereas low values were found when the clinical state of the patient was stable (FIG. 12).

Legends for the Figures and Tables:

FIG. 1: Standard Curve and Serum Dilution Curve.

The standard curve as well as the serum dilution curve are linear straight lines which pass through the origin. The lowest dilution of the standard material (1:24 with the incubation buffer mixture) reaches an optical density in the upper measuring range of the photometer (at 2500 mU) after 30 min. The standardized dilution of the sera (1:4 with an incubation buffer mixture) only exceeded the measuring range in exceptional cases.

FIG. 2. Comparison Between Serum (S) and Plasma (P), Without (−) and with (+) Addition of 10 mM EDTA The nucleosome concentration in the serum is considerably higher than in the plasma. The stability of the measured nucleosome concentration is optimized by adding 10 mM EDTA (pH 8) immediately after centrifugation (storage temperature of the samples: −20° C.).

FIG. 3: Influence of Haemolysis

When a serum with a low nucleosome content from a healthy test person is titrated with a slightly haemolysed serum, the measured signal increases dose-dependently.

FIG. 4: Influence of EDTA Addition

Sera which, after centrifugation, were stored at 4° C. and to which 10 mM EDTA was added (S1–3) after various latency periods exhibit a decrease of the measured values which depend on the delay time whereas sera to which 10 mM EDTA was immediately added after centrifugation and which subsequently were stored for various periods at 4° C. (E1–3) exhibit stable measured values (see text).

FIG. 5: Long-Term Stability

Sera with low, medium and high nucleosome concentrations exhibit a good stability over at least 6 months after adding 10 mM EDTA (pH 8) and storage at −20° C.

FIG. 6: Analytical Specificity

Non-biotinylated anti-histone antibodies are added by titration in increasing concentrations to the standard immunoreagent containing biotinylated anti-histone antibodies. The measured signal which decreases concentration-dependently into the normal range of healthy persons (100 AU) reflects the exclusive quantification of complexes which are formed from biotinylated anti-histone antibodies, nucleosomes and peroxidase-labelled DNA antibodies.

Figure 7B:
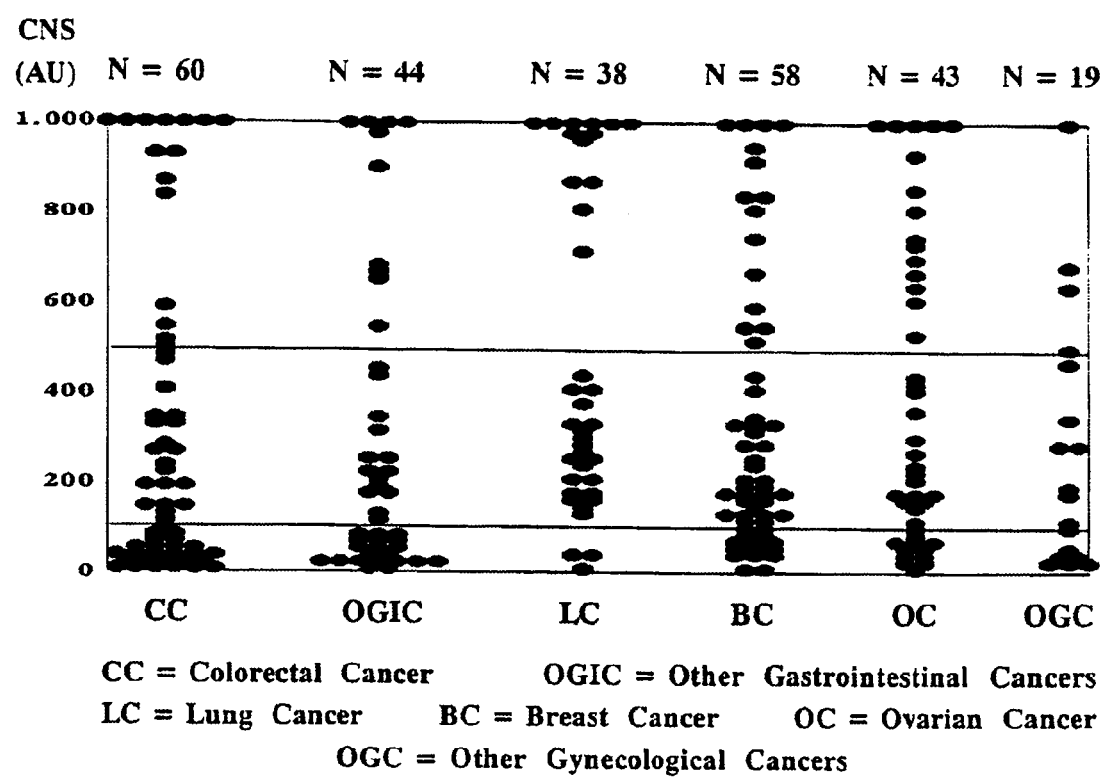
Figure 7C:
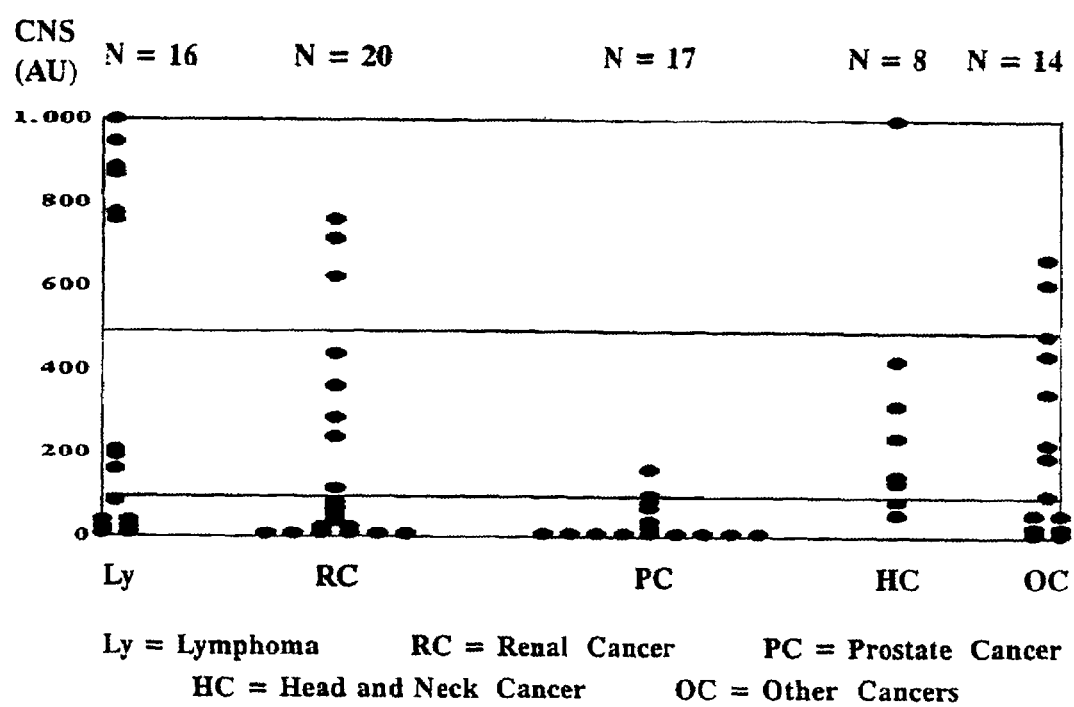

FIGS. 7a, 7b and 7c:

Distribution of Values for the Spontaneous Nucleosome Concentration in the Serum Over 95% of the measured nucleosome concentrations in the serum of healthy test persons is below 100 AU; in patients with benign diseases as well as in patients with solid tumours, all levels of values are found for the nucleosome concentrations. In this connection recognizable differences are present between various tumour types (see also text).

FIG. 8: Patient with Acute Inflammatory Disease

In this female patient with a cholangitis and cholestasis the nucleosome concentration firstly increased parallel to the Creactive protein, then decreased during antibiotic treatment which was accompanied by an improvement of the clinical state.

FIG. 9: Patient During Chemotherapy

In this patient who was being treated for a metastasising pancreatic carcinoma, the nucleosome concentration in the serum increased rapidly at the beginning of a cycle with Gemcjtabine 1000 mg/m$^2$ (day 1, 8, 15) and Cisplatin 50 mg/m$^2$ (day 1, 15) (1) and then decreased slowly. Due to a clinical progressive deterioration, a new therapy scheme with folic acid 300 mg/m$^2$ and 5-fluorouracil 500 mg/m$^2$ (on each of days 1 to 5) (2) was started. Also in this case there was firstly a rapid increase in the nucleosome concentration but there was only a partial decrease. The disease had a progressive course which was also seen in the continuous increase of CEA.

FIG. 10: Patient During Radiotherapy

In this patient with a metastasising bronchial carcinoma, there was already a substantial and rapid increase in the serum nucleosome concentration on the first day of radiation therapy (total dose 60 Gy, daily fractional dose 2.0 Gy, radiation volume 9.9 l) after an intermittent decrease. The values only decreased after several weeks which was accompanied by a radiologically demonstrable regression of the tumour. Due to an infection the nucleosome concentration increased slightly on the 40th day and then decreased again. With the occurrence of multiple metastases and a malignant pleural effusion higher nucleosome concentrations were again measured in the serum.

FIG. 11: Patient with Cerebral Insult

Three patients with different courses of the nucleosome concentration in serum after cerebral insult (stroke).

FIG. 12: Nucleosome Concentration in the Liquor

In this patient with a cerebral lymphoma infection the nucleosome concentration in the liquor was determined during the course of the disease. An increase of the liquor nucleosome values was observed when the clinical state deteriorated (days 15–19) whereas the values were low when the state was stable.

FIG. 13: Frequency Distribution of the Spontaneous Nucleosome Concentration in the Serum Median (M), mean (x), standard deviation (σ), CNS values above 100 AU and 500 AU in healthy test persons, patients with benign and malignant diseases.

FIG. 14:

Correlation of the clinical course of patients during chemotherapy with the basal nucleosome concentration in the serum determined in each case at the start of a new therapy cycle.

FIG. 15:

Correlation of the clinical course in patients during radiotherapy with a) the delay in the decrease in the serum nucleosome concentration after the maximum value had been reached during therapy and b) the minimum serum nucleosome concentration during or after conclusion of the therapy.

What is claimed is:

1. A method for determining the concentration of nucleosomes in a serum or plasma sample obtained from a human patient, said patient having a solid tumor and being subjected to a tumour therapy, said method comprising
   providing a first and second plasma sample, or a first and second serum sample, isolated from said patient after initiating said tumour therapy,
   stabilizing the first and second samples by adding an endonuclease inhibitor to each sample, and
   measuring the concentration of nucleosomes in said first and second samples.

2. The method of claim 1 wherein said tumour therapy comprises chemotherapy or radiotherapy treatment.

3. The method of claim 2 wherein the endonuclease inhibitor is EDTA.

4. The method of claim 2 further comprising a step of obtaining a plasma or serum sample from said patient before the start of said tumour therapy.

5. The method of claim 2 wherein the first plasma or serum sample is isolated from the patient within 3 hours after the first administration of the tumour therapy and a second plasma or serum sample is isolated from the patient at about 24 hours after the first administration of the tumour therapy.

6. The method of claim 1, wherein the first and second serum samples are isolated from said human patient, and further comprising incubating the first and second serum samples, separately, in a liquid phase with an anti-histone antibody and with an anti-DNA antibody, wherein one of the antibodies is bound to a solid phase before, during or after the incubation and the other antibody is a labelled antibody;
   separating the solid and liquid phases; and
   determining the label present in one of the two phases for each of said first and second serum samples and determining the relative concentration of nucleosomes in the first and second samples.

* * * * *